United States Patent [19]

Oakes et al.

[11] Patent Number: 5,437,868
[45] Date of Patent: Aug. 1, 1995

[54] PEROXYACID ANTIMICROBIAL COMPOSITION

[75] Inventors: Thomas R. Oakes, Lake Elmo; Thomas G. Boufford, Eagan, both of Minn.

[73] Assignee: Ecolab Inc., St. Paul, Minn.

[21] Appl. No.: 47,264

[22] Filed: Apr. 12, 1993

Related U.S. Application Data

[63] Continuation-in-part of Ser. No. 734,580, Jul. 23, 1991, Pat. No. 5,200,189.

[51] Int. Cl.$^6$ ............................................. A01N 37/02
[52] U.S. Cl. ................................. 424/405; 514/557; 514/558; 514/559
[58] Field of Search ................... 424/405; 514/557-559

[56] References Cited

U.S. PATENT DOCUMENTS

| | | | |
|---|---|---|---|
| 3,122,417 | 2/1964 | Blaser et al. | 23/203.5 |
| 3,248,281 | 4/1966 | Goodenough | 167/17 |
| 3,350,265 | 10/1967 | Rubinstein et al. | 167/38.6 |
| 3,514,278 | 5/1970 | Brink, Jr. | 71/67 |
| 3,895,116 | 7/1975 | Herting et al. | 424/317 |
| 4,041,149 | 8/1977 | Gaffar et al. | 424/57 |
| 4,051,058 | 9/1977 | Bowing et al. | 252/186 |
| 4,129,517 | 12/1978 | Eggensperger et al. | 252/186 |
| 4,244,884 | 1/1981 | Hutchins et al. | 260/502 R |
| 4,370,199 | 1/1983 | Orndorff | 162/161 |
| 4,404,040 | 9/1983 | Wang | 134/22.14 |
| 4,477,438 | 10/1984 | Willcockson et al. | 424/130 |
| 4,478,683 | 10/1984 | Orndorff | 162/161 |
| 4,501,681 | 2/1985 | Groult et al. | 252/174.12 |
| 4,529,534 | 7/1985 | Richardson | 252/100 |
| 4,592,488 | 6/1986 | Simon et al. | 222/94 |
| 4,613,452 | 9/1986 | Sanderson | 252/186.23 |
| 4,715,980 | 12/1987 | Lopes et al. | 252/106 |
| 4,738,840 | 4/1988 | Simon et al. | 424/51 |
| 4,802,994 | 2/1989 | Mouche et al. | 210/759 |
| 4,865,752 | 9/1989 | Jacobs | 210/791 |
| 4,900,721 | 2/1990 | Bansemir et al. | 514/25 |
| 4,906,617 | 3/1990 | Jacquet et al. | 514/24 |
| 4,917,815 | 4/1990 | Beilfuss et al. | 252/186.23 |
| 4,923,677 | 5/1990 | Simon et al. | 422/37 |
| 4,937,066 | 6/1990 | Vlock | 424/52 |
| 4,943,414 | 7/1990 | Jacobs et al. | 422/28 |
| 4,945,110 | 7/1990 | Brokken et al. | 514/517 |
| 4,996,062 | 2/1991 | Lehtonen et al. | 426/8 |
| 4,997,571 | 3/1991 | Roensch et al. | 210/698 |
| 4,997,625 | 3/1991 | Simon et al. | 422/29 |
| 5,010,109 | 4/1991 | Inoi | 514/714 |
| 5,015,408 | 5/1991 | Reuss | 252/99 |
| 5,043,176 | 8/1991 | Bycroft et al. | 426/335 |
| 5,069,286 | 12/1991 | Roensch et al. | 166/312 |
| 5,084,239 | 1/1992 | Moulton et al. | 422/22 |
| 5,114,718 | 5/1992 | Damani | 424/422 |
| 5,129,824 | 7/1992 | Keller | 433/215 |
| 5,130,124 | 7/1992 | Merianos et al. | 424/53 |
| 5,139,788 | 8/1992 | Schmidt | 424/616 |
| 5,176,899 | 1/1993 | Montgomery | 424/50 |
| 5,200,189 | 4/1993 | Oakes et al. | 424/405 |

FOREIGN PATENT DOCUMENTS

| | | |
|---|---|---|
| 0195619A2 | 9/1986 | European Pat. Off. . |
| 0233731A2 | 8/1987 | European Pat. Off. . |
| 0461700 | 12/1991 | European Pat. Off. . |
| 0569066 | 11/1993 | European Pat. Off. . |
| 3543500 | 6/1987 | Germany . |

OTHER PUBLICATIONS

Parker et al., Preparation, Characterization and Polarographic Behavior of Long-Chain Aliphatic Acids.
Parker et al., Desinfectants Based on Peracid-Splitting Compounds.
Eggensperger, Desinfectants Based on Peracid-Splitting Compounds.
Neo-Fat © Fatty Acids (Armak Chemicals).
Emery © Fatty and Dibasic Acids (Emery).

*Primary Examiner*—Thurman K. Page
*Assistant Examiner*—Neil Levy
*Attorney, Agent, or Firm*—Merchant, Gould, Smith, Edell Welter & Schmidt

[57] ABSTRACT

A peroxyacid antimicrobial concentrate and use composition is provided comprising a $C_5$ peroxyacid in combination with a $C_1$-$C_4$ peroxyacid, a $C_6$-$C_{18}$ peroxyacid, or mixtures thereof. The combination of these peracids produces a synergistic effect, providing a much more potent biocide than can be obtained by using these components separately. Other components can be added to the composition such as hydrotrope coupling agents, stabilizers, etc. An effective antimicrobial use solution is formed at low concentrations when the concentrate composition is diluted with water. Sanitizing of substantially fixed, "in-place" processing lines in dairies, breweries, and other food processing operations is one utility of the composition.

18 Claims, No Drawings

PEROXYACID ANTIMICROBIAL COMPOSITION

This patent application is a continuation-in-part of U.S. Ser. No. 07/734,580, filed Jul. 23, 1991, and now U.S. Pat. No. 5,200,189.

FIELD OF THE INVENTION

The invention relates generally to antimicrobial or biocidal compositions. More particularly, the invention relates to peroxyacid antimicrobial concentrates and use solutions which can sanitize surfaces, facilities and equipment found in food manufacture and food processing and food service industries, and typically hard non-porous surfaces in the health care industry.

BACKGROUND OF THE INVENTION

Antimicrobial compositions are particularly needed in the food and beverage industries to clean and sanitize processing facilities such as pipelines, tanks, mixers, etc. and continuously operating homogenation or pasteurization apparatus. Sanitizing compositions have been formulated in the past to combat microbial growth in such facilities. For example, Wang, U.S. Pat. No. 4,404,040, teaches a short chain fatty acid sanitizing composition comprising an aliphatic short chain fatty acid, a hydrotrope solubilizer capable of solubilizing the fatty acid in both the concentrate and use solution, and a hydrotrope compatible acid so that the use solution has a pH in the range of 2.0 to 5.0.

Peroxy-containing compositions are known for use in the production of microbicidal agents. One such composition is disclosed in Bowing et al., U.S. Pat. No. 4,051,059 containing peracetic acid, acetic acid or mixtures of peracetic and acetic acid, hydrogen peroxide, anionic surface active compounds such as sulfonates and sulfates, and water.

Peracetic acid, generally using some concentrations of acetic acid and hydrogen peroxide has been shown to be a good biocide, but only at fairly high concentrations (generally greater than 100 parts peracetic acid per million (ppm)). Similarly, peroxyfatty acids have also been shown to be biocidal, but only at high concentrations (greater than 200 ppm), such as in the composition disclosed in European Patent Application No. 233,731. Peroxyacetic acid is a good biocide, but it possesses a very strong odor, especially in the concentrate. For general use applications, for example, as a floor disinfectant or as an automatic dish wash destainer or sanitizer, it is desirable to have a product with low odor. Thus, it is desirable to obtain a low odor peroxy antimicrobial formulation that is at least as effective as peroxyacetic acid.

Antimicrobial compositions having low use concentrations (less than 100 ppm) which effectively kill microbes are particularly desirable. Low concentrations minimize use cost, surface corrosion, odor, carryover of biocide into foods and potential toxic effects to the user. Therefore, a continuing need exists to provide such an antimicrobial composition for use in food processing, food service and health care facilities. In contrast to the prior art, the composition of the present invention has the unique advantage of having unanticipated excellent antimicrobial or biocidal activity at low level use concentrations.

SUMMARY OF THE INVENTION

The invention includes a peroxyacid antimicrobial concentrate and diluted end use composition comprising an effective biocidal amount of either a $C_1$-$C_4$ peroxyacid, and an effective biocidal amount of a $C_6$-$C_{18}$ peroxyacid. The invention also includes a concentrate composition comprising the combination of an effective biocidal amount of a $C_5$ peroxyacid with an effective biocidal amount of a $C_1$-$C_4$ peroxyacid or a $C_6$-$C_{18}$ peroxyacid. All three components of a $C_1$-$C_4$ peroxyacid, $C_5$ peroxyacid, and $C_6$-$C_{18}$ peroxyacid can also be combined in the composition of the invention.

The above concentrate compositions can be diluted with a major proportion of water to form antimicrobial sanitizing use solutions having a pH in the range of about 2 to 8. When a $C_1$-$C_4$ peroxyacid is used, its concentration is at least about 10 ppm, preferably about 10 to 75 ppm. When a $C_5$ peroxyacid is used, its concentration is at least about 10 ppm, preferably about 20 to 100 ppm. When a $C_6$-$C_{18}$ peroxyacid is used, its concentration is at least about 1 ppm, preferably about 1 to 25 ppm. Other components may be added such as a hydrotrope coupling agent for solubilizing the peroxyfatty acid in the concentrate form and when the concentrate composition is diluted with water.

In contrast to the prior art, we have discovered that at a low pH (e.g. preferably less than 5), $C_6$-$C_{18}$ peroxyacids such as peroxyfatty acids are potent biocides at low levels. When used in combination with a $C_1$-$C_4$ peroxyacid such as peroxyacetic acid or a $C_5$ peroxyacid such as peroxyglutaric acid, a synergistic effect is obtained, providing a much more potent biocide than can be obtained by using these components separately. This means that substantially lower concentrations of biocide can be used to obtain equal cidal effects, leading to lower costs of the product and less potential for corrosion.

For example, we now have shown that combinations of peroxyglutaric acid and peroxyoctanoic acid possess surprisingly good bacterial kill properties at low concentrations, and both the use solution and concentrated composition possess low odor. This composition can be made by adding a mixture of glutaric acid and octanoic acid to a solution of hydrogen peroxide in the presence of a stabilizer and a solubilizer. We have demonstrated, using $^{13}C$ NMR spectroscopy, that both peroxyacids form in the above mixtures. That is, by merely adding the parent carboxylic acids to a properly stabilized hydrogen peroxide system, the peroxyacids can be formed in sufficient quantity to give good bacterial kill at relatively low concentrations (e.g., about 50 ppm total peroxyacids by titration). From antimicrobial testing, we know that mixtures of peroxyglutaric acid and peroxyoctanoic acid are surprisingly effective, and that only small amounts of peroxyoctanoic acid are needed to greatly enhance the activity of a peroxyglutaric acid formula. The resulting activity is greater than the arithematic sum of the activity of each material separately.

As the term is used herein, a $C_6$-$C_{18}$ peroxyacid (or peracid) is intended to mean the product of the oxidation of a $C_6$-$C_{18}$ acid such as a fatty acid, or a mixture of acids, to form a peroxyacid or mixture of oxidized acids having from about 6 to 18 carbon atoms per molecule. The term $C_1$-$C_4$ peroxyacid is intended to mean the product of the oxidation of a $C_1$-$C_4$ carboxylic acid, or a mixture of acids thereof resulting in a single $C_{1-4}$ peroxyacids or a mixture of such peroxyacids. This includes both simple and substituted $C_1$-$C_4$ carboxylic acids. The term $C_5$ peroxyacid is intended to mean the product of the oxidation of a $C_5$ carboxylic acid.

A method of sanitizing a surface, facilities or equipment comprises the steps of contacting the surface, facilities or equipment with the use solution made from the above concentrate compositions of the invention at a temperature in the range of about 4° to 60° C. The composition is then circulated or left in contact with the facilities or equipment for a time sufficient to sanitize (generally at least 30 seconds) and the composition is thereafter drained or removed from the facilities or equipment.

One aspect of the invention are the novel, antimicrobial concentrate compositions which are capable of being diluted with a major proportion of water to form sanitizing use solutions. A further aspect of the invention is the aqueous antimicrobial sanitizing use solutions which are particularly suited for "in-place" cleaning applications. Another aspect of the invention is a method of employing the use solutions in the cleaning or sanitizing of various process facilities or equipment as well as other surfaces.

DETAILED DESCRIPTION OF THE INVENTION

The invention resides in peroxyacid antimicrobial concentrate and use compositions comprising various combinations of a $C_5$ peroxyacid, with a $C_1$-$C_4$ peroxyacid, or a $C_6$-$C_{18}$ peroxyacid. We have found that combining these acids produces an antimicrobial effect that is greater than the arithmatic sum of the activity of the individual acids, antimicrobial activity, producing a much more potent biocide than can be obtained by using these components separately. The concentrate compositions can be diluted with a major proportion of water to form antimicrobial sanitizing use solutions having a pH in the range of about 2 to 8. The sanitizing use solutions can be used effectively to clean or sanitize facilities and equipment used in the food processing, food service and health care industries.

Peracids

The present invention is based upon the surprising discovery that when a $C_5$ peroxy acid is combined with a $C_6$-$C_{18}$ peroxyacid or a $C_1$-$C_4$ peroxyacid, a synergistic effect is produced and greatly enhanced antimicrobial activity is exhibited when compared to the $C_5$ peroxyacid, the $C_6$-$C_{18}$ peroxyacid or the $C_1$-$C_4$ peroxyacid alone. The present composition blends can effectively kill microorganisms (e.g., a 5 $\log_{10}$ reduction in 30 seconds) at a concentration level below 100 ppm and as low as 20 ppm of the peracid blend.

The preferred $C_5$ peroxyacid for use in the present invention is peroxyglutaric acid which is made from glutaric acid having the formula $CO_3H(CH_2)_3CO_3H$. The peroxyglutaric acid can be monoperoxy, diperoxy or mixtures of monoperoxy and diperoxy acids. Aqueous solutions of peroxyglutaric acid containing an excess of hydrogen peroxide ($H_2O_2$) and, if appropriate, also a stabilizer known for $H_2O_2$ can be employed in the invention. Such solutions contain about 1 to 60 wt-% of peroxyglutaric acid, about 1 to 50 wt-% of $H_2O_2$, about 0 to 50 wt-% of glutaric acid, and the remainder water. About 0.01 to 2 wt-% of a stabilizer can be used such as urea or 2,3-pyridinedicarboxylic acid and/or 2,6-pyridinedicarboxylic acid. We have found that these peroxyglutaric acid materials have surprising solubility in aqueous systems and low odor.

A variety of $C_6$-$C_{18}$ peroxyacids may be employed in the composition of the invention such as peroxyfatty acids, monoperoxy- or diperoxydicarboxylic acids, and peroxy aromatic acids. The $C_6$-$C_{18}$ peroxyacids employed in the present invention may be structurally represented as follows: $R_1$—$CO_3H$, wherein $R_1$ is a hydrocarbon moiety having from about 5 to 17 carbon atoms (a $C_8$ peroxyacid is generally represented structurally as $C_7$—$CO_3H$). $R_1$ may have substituents in the chain, e.g., —OH, $CO_2H$, or heteroatoms (e.g., —O— as in alkylether carboxylic acids), as long as the antimicrobial properties of the overall composition are not significantly affected. The "$R_1$" substituents or heteroatoms may change the overall acidity (i.e., pKa) of the carboxylic acids herein described. Such modification is within the contemplation of the present invention provided the advantageous antimicrobial performance is maintained. Furthermore, $R_1$ may be linear, branched, cyclic or aromatic. Preferred hydrocarbon moieties (i.e. preferred $R_1$'s) include linear, saturated, hydrocarbon aliphatic moieties having from 7 to 11 carbon atoms (or 8 to 12 carbon atoms per molecule).

Specific examples of suitable $C_6$-$C_{18}$ carboxylic fatty acids which can be reacted with hydrogen peroxide to form peroxyfatty acids include such saturated fatty acids as hexanoic ($C_6$), enanthic (heptanoic) ($C_7$), caprylic (octanoic) ($C_8$), perlargonic (nonanoic) ($C_9$), capric (decanoic) ($C_{10}$), undecyclic (undecanoic) ($C_{11}$), lauric (dodecanoic) ($C_{12}$), tridectic (tridecanoic) ($C_{13}$), myristic (tetradecanoic) ($C_{14}$), palmitic (hexadecanoic) ($C_{16}$), and stearic (octodecanoic) ($C_{18}$). These acids can be derived from both natural and synthetic sources. Natural sources include animal and vegetable fats or oils which should be fully hydrogenated. Synthetic acids can be produced by the oxidation of petroleum wax. Particularly preferred peroxyfatty acids for use in the composition of the invention are linear monoperoxy aliphatic fatty acids such as peroxyoctanoic acid, peroxydecanoic acid, or mixtures thereof.

Other suitable $C_6$-$C_{18}$ peroxyacids are derived from the oxidation of dicarboxylic acids and aromatic acids. Suitable dicarboxylic acids include adipic acid ($C_6$) and sebacic acid ($C_{10}$). Examples of a suitable aromatic acid include benzoic acid, phthalic acid, terephthalic acid, hydroxy benzoic acid, etc. These acids can be reacted with hydrogen peroxide to form the peracid form suitable for use in the composition of the invention. Preferred peracids in this group include monoperoxy- or diperoxyadipic acid, monoperoxy- or diperoxysebacic acid, and peroxybenzoic acid.

The $C_1$-$C_4$ peroxyacid component can be derived from a $C_1$-$C_4$ carboxylic acid or dicarboxylic acid by reacting the acid with hydrogen peroxide. Examples of suitable $C_1$-$C_4$ carboxylic acids include acetic acid, propionic acid, glycolic acid, and succinic acid. Preferable $C_1$-$C_4$ peroxycarboxylic acids for use in the composition of the invention include peroxyacetic acid, peroxypropionic acid, peroxyglycolic acid, peroxysuccinic acid, or mixtures thereof.

The above peroxyacids provide antibacterial activity against a wide variety of microorganisms, such as gram positive (e.g., *Staphylococcus aureus*) and gram negative (e.g., *Escherichia coli*) microorganisms, yeast, molds, bacterial spores, etc. When combined, the above peroxyacids have greatly enhanced activity compared to a $C_1$-$C_4$ peroxyacid, a $C_5$ peroxyacid, or a $C_6$-$C_{18}$ peroxyacid alone.

The antimicrobial concentrates of the present invention can comprise about 0 to 10 wt-%, preferably about 0.05 to 5 wt-%, and most preferably about 0.1 to 2 wt-% of a $C_6$-$C_{18}$ peroxyacid; about 0 to 30 wt-%, preferably about 1 to 25 wt-%, and most preferably about 5 to 20 wt-% of a $C_5$ peroxyacid; and about 0 to 25 wt-%, preferably about 0.5 to 20 wt-%, and most preferably about 1 to 15 wt-% of a $C_1$-$C_4$ peroxyacid. One concentrate composition preferably has a weight ratio of $C_1$-$C_4$ peroxyacid to $C_6$-$C_{18}$ peroxyacid of about 15:1 to 3:1. Another concentrate composition preferably has a weight ratio of $C_5$ peroxyacid to $C_6$-$C_{18}$ peroxyacid of about 20:1 to 2:1. A further concentrate composition has a weight ratio of $C_5$ peroxyacid to $C_1$-$C_4$ peroxyacid of about 10:1 to 1:10. The concentrate compositions contain sufficient acid so that the end use solution has a pH of about 2 to 8, preferably about 3 to 7. Some acidity may come from an inert acidulant which may be optionally added (e.g., phosphoric acid).

The peracid components used in the composition of the invention can be produced in a simple manner by mixing a hydrogen peroxide ($H_2O_2$) solution with the desired amount of carboxylic acid or acid blend. With the higher molecular weight fatty acids, a hydrotrope coupler may be required to fully solubilize the fatty acid. The $H_2O_2$ solution also can be added to previously made peroxyacids such as peroxyacetic acid, peroxyglutaric acid or various peroxy fatty acids to produce the peroxyacid composition of the invention. The concentrates can contain about 1 to 50 wt-%, preferably about 5 to 25 wt-% of hydrogen peroxide.

The concentrate compositions can further comprise a free $C_6$-$C_{18}$ carboxylic acid, a free $C_5$ carboxylic acid, a free $C_1$-$C_4$ carboxylic acid, or mixtures thereof. The free acids will preferably correspond to the starting materials used in the preparation of the peroxyacid components. The free $C_6$-$C_{18}$ carboxylic acid is preferably linear and saturated, has 8 to 12 carbon atoms per molecule, and can also comprise a mixture of acids. The free $C_6$-$C_{18}$ carboxylic acid, free $C_5$ carboxylic acid, and free $C_1$-$C_4$ carboxylic acid can be present as a result of an equilibrium reaction with the hydrogen peroxide to form the peroxyacids.

Optional Components

Various optional materials may be added to the composition of the invention to help solubilize the fatty acids, restrict or enhance the formation of foam, to control hard water, to stabilize the composition, or to further enhance the antimicrobial activity of the composition.

The compositions of the invention can contain a surfactant hydrotrope coupling agent or solubilizer that permits blending both fatty acids and short chain perfatty acids in aqueous liquids. Functionally speaking, the suitable couplers which can be employed are nontoxic and retain the fatty acid and the perfatty acid in aqueous solution throughout the temperature range and concentration to which a concentrate or any use solution is exposed.

Any hydrotrope coupler may be used provided it does not react with the other components of the composition or negatively affect the antimicrobial properties of the composition. Representative classes of hydrotropic coupling agents or solubilizers which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters) and $C_8$-$C_{10}$ alkyl glucosides. Preferred coupling agents for use in the present invention include n-octanesulfonate, available as NAS 8D from Ecolab, and the commonly available aromatic sulfonates such as the alkyl benzene sulfonates (e.g. xylene sulfonates) or naphthalene sulfonates.

Some of the above hydrotropic coupling agents independently exhibit antimicrobial activity at low pH. This adds to the efficacy of the present invention, but is not the primary criterion used in selecting an appropriate coupling agent. Since it is the presence of perfatty acid in the protonated neutral state which provides biocidal activity, the coupling agent should be selected not for its independent antimicrobial activity but for its ability to provide effective interaction between the substantially insoluble perfatty acids described herein and the microorganisms which the present compositions control.

The hydrotrope coupling agent can comprise about 0.1 to 30 wt-%, preferably about 1 to 20 wt-%, and most preferably about 2 to 15 wt-% of the concentrate composition.

Compounds such as mono, di and trialkyl phosphate esters may be added to the composition to suppress foam. Such phosphate esters would generally be produced from aliphatic linear alcohols, there being from 8 to 12 carbon atoms in the aliphatic portions of the alkyl phosphate esters. Alkyl phosphate esters possess some antimicrobial activity in their own right under the conditions of the present invention. This antimicrobial activity also tends to add to the overall antimicrobial activity of the present compositions even though the phosphate esters may be added for other reasons. Furthermore, the addition of nonionic surfactants would tend to reduce foam formation herein. Such materials tend to enhance performance of the other components of the composition, particularly in cold or soft water. A particularly useful nonionic surfactant for use as a defoamer is nonylphenol having an average of 12 moles of ethylene oxide condensed thereon, it being encapped with a hydrophobic portion comprising an average of 30 moles of propylene oxide.

A variety of chelating agents can be added to the composition of the invention to enhance biological activity, cleaning performance and stability of the peroxyacids. For example, 1-hydroxyethylidene-1,1-diphosphonic acid commercially available from the Monsanto Company under the designation "DEQUEST 2010" has been found to be effective. Other effective chelating agents include 1,6 pyridine dicarboxylic acid. Chelating agents can be added to the present composition to control or sequester hardness ions such as calcium and magnesium. In this manner both detergency and sanitization capability can be enhanced.

Other materials which are sufficiently stable at the low pH contemplated by the present composition may be added to the composition to impart desirable qualities depending upon the intended ultimate use. For example, phosphoric acid ($H_3PO_4$) can be added to the composition of the invention. Additional compounds can be added to the concentrate (and thus ultimately to the use solution) to change its color or odor, to adjust its viscosity, to enhance its thermal (i.e., freeze-thaw) stability or to provide other qualities which tend to make it more marketable.

The compositions of the invention can be made by combining by simple mixing at least two of a $C_6$-$C_{18}$ peroxyacid, a $C_1$-$C_4$ peroxyacid, and a $C_5$ peroxyacid. These compositions could be formulated with preformed peroxyacids. A preferred composition of the invention can be made by mixing a $C_5$ carboxylic acid with a $C_1$-$C_4$ carboxylic acid or an aliphatic $C_6$-$C_{18}$ carboxylic acid, optionally a coupler and/or a stabilizer, and reacting this mixture with hydrogen peroxide. A stable equilibrium mixture is produced containing a $C_5$ peroxyacid and a $C_1$-$C_4$ peroxyacid or an aliphatic $C_6$-$C_{18}$ peroxyacid by allowing the mixture to stand for from one to seven days at 15° C. to 25° C. As with any aqueous reaction of hydrogen peroxide with a free carboxylic acid, this gives a true equilibrium mixture. In this case, the equilibrium mixture will contain hydrogen peroxide, an unoxidized $C_5$ carboxylic acid, an unoxidized $C_1$-$C_4$ carboxylic acid or an unoxidized aliphatic $C_6$-$C_{18}$ carboxylic acid, a $C_5$ peroxyacid, a $C_1$-$C_4$ peroxyacid or an aliphatic $C_6$-$C_8$ peroxyacid, and optionally various couplers and/or stabilizers.

By using the above approach, the compositions of the invention can be formulated by merely mixing readily available raw materials, e.g., glutaric acid, acetic acid, hydrogen peroxide and fatty acid. By allowing solution time for equilibrium to be obtained, the product containing the active biocides is obtained. In varying the ratio of $C_5$ carboxylic acid to $C_1$-$C_4$ carboxylic acid or $C_6$-$C_{18}$ carboxylic acid, it is easy to vary the ratio of $C_5$ peroxyacid to $C_1$-$C_4$ peroxycarboxylic acid or $C_6$-$C_{18}$ peroxyacid.

Concentrate and Use Compositions

The present invention contemplates a concentrate composition which is diluted to a use solution prior to its utilization as a sanitizer. Primarily for reasons of economics, the concentrate would normally be marketed and the end user would dilute the concentrate with water to a use solution. Preferred antimicrobial concentrate compositions comprise about 1 to 25 wt-%, preferably about 5 to 20 wt-%, of a $C_5$ peroxyacid, about 0.01 to 10 wt-%, preferably about 0.05 to 5 wt-%, of a $C_6$-$C_{18}$ peroxyfatty acid, and/or about 0.1 to 25 wt-%, preferably about 0.5 to 20 wt-%, of a $C_1$-$C_4$ peroxyacid. The concentrate compositions can further include about 0.1 to 30 wt-% of a hydrotrope coupling agent, and about 1 to 50 wt-% of hydrogen peroxide. Other acidulants may optionally be employed in the compositions such as phosphoric acid. All three of the above peroxyacids may be combined together in the above amounts to form an effective antimicrobial concentrate composition.

The level of active components in the concentrate composition is dependent upon the intended dilution factor and desired acidity in the use solution. The $C_6$-$C_{18}$ peroxyacid component is generally obtained by reacting a $C_6$-$C_{18}$ carboxylic acid with hydrogen peroxide in the presence of a $C_1$-$C_4$ carboxylic acid and/or a $C_5$ carboxylic acid. The resulting concentrate is diluted with water to provide the use solution. Generally, a dilution of 1 fluid oz. to 4 gallons (i.e. dilution of 1 to 500 by volume) or to 8 gallons (i.e. dilution of 1 to 1,000 by volume) of water can be obtained with 2% to 20% total peracids in the concentrate. Higher use dilution can be employed if elevated use temperature (greater than 20° C.) or extended exposure time (greater than 30 seconds) are also employed.

In its intended end use, the concentrate is diluted with a major proportion of water and used for purposes of sanitization. The typical concentrate composition described above is diluted with available tap or service water to a formulation of approximately 1 oz. concentrate to 8 gallons of water. Aqueous antimicrobial sanitizing use solutions can comprise at least about 1 part per million (ppm), preferably about 10 to 100 ppm, of a $C_5$ peroxyacid, at least about 1 ppm, preferably about 2 to 10 ppm of a $C_6$-$C_{18}$ peroxyacid, and/or at least about 10 ppm, preferably about 20 to 50 ppm of a $C_1$-$C_4$ peroxyacid. Any two of the above peracids may be present in the use solution or all three may be present, depending on the concentrate composition ingredients. In a preferred composition, the weight ratio of $C_6$-$C_{18}$ peroxyacid to $C_5$ peroxyacid ranges from about 0.01 to 0.5 parts, preferably about 0.02 to 0.2 parts, of $C_6$-$C_{18}$ peroxyacid per part of $C_5$ peroxyacid. Preferably the total peracid concentration in the use solution is less than about 75 ppm, and most preferably between about 5 to 50 ppm. Higher levels of peracids can be employed in the use solution to obtain disinfecting or sterilizing results.

The aqueous use solution can further comprise at least about 1 ppm, preferably about 2 to 20 ppm, of a hydrotrope coupling agent, and at least about 1 ppm, preferably about 2 to 200 ppm of hydrogen peroxide. The use solution can also comprise at least about 1 ppm, preferably about 2 to 200 ppm of a free $C_6$-$C_{18}$ carboxylic acid, a free $C_5$ carboxylic acid, a free $C_1$-$C_4$ carboxylic acid, or mixtures thereof. The aqueous use solutions have a pH in the range of about 2 to 8, preferably about 3 to 7.

Methods of Use

As noted above, the present composition is useful in the cleaning or sanitizing of processing facilities or equipment in the food service, food processing or health care industries. Examples of process facilities in which the composition of the invention can be employed include a dairy milk line, a continuous brewing system, food processing lines such as pumpable food systems and beverage lines, etc. Food service wares can also be sanitized with the composition of the invention. The composition is also useful in sanitizing or disinfecting solid surfaces such as floors, counters, furniture, medical tools and equipment, etc., found in the health care industry. Such surfaces often become contaminated with liquid body spills such as blood, other hazardous body fluids or mixtures thereof.

Generally, the actual cleaning of the in-place system or other surface (i.e., removal of unwanted offal therein) is accomplished with a different material such as a formulated detergent which is introduced with heated water. After this cleaning step, the instant sanitizing composition would be applied or introduced into the system at a use solution concentration in unheated, ambient temperature water. The present sanitizing composition is found to remain in solution in cold (e.g., 40° F./4° C.) water and heated (e.g., 140° F./60° C.) water. Although it is not normally necessary to heat the aqueous use solution of the present composition, under some circumstances heating may be desirable to further enhance its antimicrobial activity.

A method of sanitizing substantially fixed in-place process facilities comprises the following steps. The use solution composition of the invention is introduced into the process facilities at a temperature in the range of about 4° to 60° C. After introduction, the use solution is circulated throughout the system for a time sufficient to sanitize the process facilities (i.e., to kill undesirable microorganisms). After the system has been sanitized by means of the use solution composition, the use solution is drained from the system. Upon completion of the sanitizing step, the system optionally may be rinsed with other materials such as potable water. The composition is preferably circulated through the process facilities for 10 minutes or less and allowed to drain without further treatment.

The composition may also be employed by dipping food processing equipment into the use solution, soaking the equipment for a time sufficient to sanitize the equipment, and draining excess solution off the equipment. The composition may be further employed by spraying or wiping food processing surfaces with the use solution, keeping the surfaces wet for a time sufficient to sanitize the surfaces, and removing excess solution by draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric which has become contaminated. The composition is contacted with any of the above contaminated surfaces or items at use temperatures in the range of about 4° to 60° C., for a period of time effective to sanitize, disinfect, or sterilize the surface or item. For example, the concentrate composition can be injected into the wash or rinse water of a laundry machine and contacted with contaminated fabric for a time sufficient to sanitize the fabric. Excess solution can then be removed by rinsing or centrifuging the fabric.

As the term "sanitizing" is used in the method of the instant invention, it means a reduction in the population numbers of undesirable microorganisms by about 5 powers of 10 or greater (i.e., at least 5 orders of magnitude) after a 30 second exposure time. It is to be emphasized that the instant use solution provides cleaning as well as sanitizing performance although its primary utility is sanitizing. The composition may also be used to achieve disinfection or sterilization (i.e., elimination of all microorganisms) by employing higher levels of peracids in the use solution.

The following Examples which contain a best mode, are intended to illustrate the above invention and should not be construed as to narrow its scope. One skilled in the art will readily recognize that these Examples suggest many other ways in which the present invention could be practiced. Examples 1-14 demonstrate cooperation between $C_{1-4}$ peracids and $C_{6-18}$ peracids. Examples 15 and 16 demonstrate the superiority of a $C_5$ peracid in combination with either a $C_{1-4}$ peracid, or a $C_{6-18}$ peracid. Examples 17-32 demonstrate the efficacy of the blends preparative information, stability, and aging tests.

Example 1

Experiments were conducted to determine the antimicrobial efficacy of pure peroxyacids. Table I below demonstrates the antimicrobial efficacy of pure peroxyacids at very low levels when exposed to *S. aureus* and *E. coli*. The peroxyacids listed in Table I were tested by diluting them in 0.05M citrate buffer made in distilled water and were exposed to the bacteria for 30 seconds at 20° C. As Table I indicates, the diperoxyacids were somewhat less active than the peroxyfatty acids. Peroxydecanoic acid was very effective at very low levels against *S. aureus*, but higher levels were required to be effective against *E. coli*. Higher levels were also required at pH 5.

TABLE I

| Comparison of Cidal Activity of Peroxyacids | | | |
| --- | --- | --- | --- |
| | | Minimum concentration required for 5 log reduction (ppm)[a] | |
| Peroxyacid | pH | *S. aureus* | *E. coli* |
| Peroxyhexanoic | 3.5 | 15 | 15 |
| ($C_6$) | 5.0 | 20 | 15 |
| Diperoxyadipic | 3.5 | >50 | 40 |
| ($C_6$) | 5.0 | >60 | 35 |
| Peroxyoctanoic | 3.5 | 5 | 5 |
| ($C_8$) | 5.0 | 10 | 15 |
| Peroxydecanoic | 3.5 | 3 | 10 |
| ($C_{10}$) | 5.0 | 1 | 30 |
| Diperoxysebacic | 3.5 | 15 | 15 |
| ($C_{10}$) | 5.0 | 10 | 50 |

[a]Peroxyacids tested at 5-ppm increments, or at 1, 3, and 5 ppm where appropriate.

In Table II below, the degree of antimicrobial kill resulting from a cooperation between the $C_2$ and $C_3$ peroxyacids when combined with $C_8$ and $C_{10}$ peroxyfatty acids is shown. As Table II shows, there was little or no antimicrobial activity when the $C_2$ and $C_3$ peroxyacids and the $C_8$ and $C_{10}$ peroxyfatty acids were tested alone. However, when a $C_2$ or $C_3$ peroxyacid was combined with a $C_8$ or $C_{10}$ peroxyfatty acid, the bacterial kill of *E. coli* surprisingly increased. These tests were conducted at pH 4.5 or 5 (see Table II).

TABLE II

| Cooperative Interaction of Peroxyacids | | | | |
| --- | --- | --- | --- | --- |
| $C_2$ [Peroxyacetic] (ppm) | $C_3$ [Peroxypropionic] (ppm) | $C_8$ [Peroxyoctanoic] (ppm) | $C_{10}$ [Peroxydecanoic] reduction (ppm) | Microbial Population Log Reduc. |
| 25 | | 0 | | 0[a] |
| 0 | | 5 | | 0.1[a] |
| 25 | | 5 | | 3.8[a] |
| | 25 | 0 | | 0.3[b] |
| | 0 | 6 | | 0.1[b] |
| | 25 | 6 | | 3.9[b] |
| 30 | | | 0 | 0.7[a] |
| 0 | | | 6 | 0[a] |
| 30 | | | 6 | 2.6[a] |

[a]*E. coli*, pH 5, distilled water
[b]*E. coli*, pH 4.5, 500 ppm hard water

Examples 2-6

A two-component system containing peracetic acid and perfatty acid was formulated and tested to determine its sanitizing activity over just a peracetic acid system. Table III shows premixes 1 and 2 used in making the composition. The premixes were both made with $H_2O_2$ (35% solution), acetic acid, Dequest 2010, and with/without $H_3PO_4$. Premix 1 was made about 5 months before premix 2. To each premix was added NAS 8D, a $C_8$ fatty acid or Emery 658 as shown in Table IV to complete the formulation of Examples 2-5. Example 6 was formulated as a control and had no fatty acid.

TABLE III

Peracid Premixes

| | Wt-% Component | |
|---|---|---|
| Component | Premix 1 | Premix 2 |
| $H_2O_2$ (35%) | 75.0 | 35.0 |
| Acetic acid (glacial) | 24.0 | 35.0 |
| Dequest 2010 | 1.0 | 1.0 |
| $H_3PO_4$ (85%) | — | 29.0 |

TABLE IV

Perfatty Acid/Peracetic Acid Formulations

| | Wt-% Ingredient | | | | |
|---|---|---|---|---|---|
| Ingredient | Ex. 2 | Ex. 3 | Ex. 4 | Ex. 5 | Ex. 6 |
| Premix 1 | 80.0 | — | 80.0 | — | — |
| Premix 2 | — | 80.0 | — | 80.0 | — |
| NAS 8D | 10.0 | 10.0 | 10.0 | 10.0 | — |
| $C_8$ Fatty Acid | 10.0 | 10.0 | — | — | — |
| Emery 658 | — | — | 10.0 | 10.0 | — |
| Acetic Acid (Glacial) | — | — | — | — | 24.0 |
| $H_2O_2$ (35%) | — | — | — | — | 75.0 |
| Dequest 2010 | — | — | — | — | 1.0 |

Table V shows the sanitizing activity measured from each formulation of Examples 2-5 at 50, 100, or 150 ppm peracetic acid against *S. aureus* (Example 6 is a control).

TABLE V

Sanitizing Efficacy of Perfatty Acid/
Peracetic Acid System vs.
Sanitizing Efficacy of Peracetic Acid System

| Example | Total Peracid[a] (Percent) | Fatty Acid (Percent) | Test Concentration[a] (ppm) | Test pH | Log[b] Reduction |
|---|---|---|---|---|---|
| 2 | 7.69 | 10.0 | 150 | 3.53 | >7.06 |
| | | | 100 | 3.64 | >7.06 |
| | | | 50 | 3.83 | >7.06 |
| 3 | 11.21 | 10.0 | 150 | 2.71 | >7.06 |
| | | | 100 | 2.80 | >7.06 |
| | | | 50 | 3.08 | >7.06 |
| 4 | 9.08 | 10.0 | 150 | 3.64 | >7.06 |
| | | | 100 | 3.65 | >7.06 |
| | | | 50 | 3.85 | >7.06 |
| 5 | 10.92 | 10.0 | 150 | 2.68 | >7.06 |
| | | | 100 | 2.77 | >7.06 |
| | | | 50 | 3.10 | >7.06 |
| 6 | 10.40 | — | 150 | 3.56 | >7.06 |
| | | | 100 | 3.68 | 3.89 |
| | | | 50 | 3.93 | NMA[c] |

[a]As peracetic acid
[b]Average of duplicate testing against *S. aureus*.
[c]No measurable activity.

Extremely good kill (>7 log reduction) was obtained with or without $H_3PO_4$ in the perfatty acid formulations of Examples 2-6. The two component system of $C_8$ fatty acid or Emery 658 in combination with peracetic acid (Example 2-5 had significantly better kill than the peracetic acid system alone (Example 6) at a test concentration of 50 to 100 ppm. No activity was measured at 50 ppm with the single peracetic acid system of Example 6.

Example 7-10

The effect of alkyl chain length on antimicrobial efficacy of perfatty acids was determined for percaprylic ($C_8$) acid, percapric ($C_{10}$) acid and a percaprylic/percapric (3:1) perfatty acid mixture using the compositions of Examples 7-8 summarized in Table VI below.

TABLE VI

| | Wt-% of Ingredient | | | |
|---|---|---|---|---|
| Ingredient | Ex. 7 | Ex. 8 | Ex. 9 | Ex. 10 |
| Percaprylic ($C_8$) Acid | 1 | — | — | — |
| Percapric ($C_{10}$) Acid | — | 1 | — | — |
| $C_8$ + $C_{10}$ (3:1) Perfatty Acid | — | — | 1 | — |
| Acetic Acid | 10 | 10 | 10 | 10 |
| Water | 84 | 84 | 84 | 85 |
| NAS 8D | 5 | 5 | 5 | 5 |

The antimicrobial efficacy of Examples 7-10 are summarized in Table VII below. Examples 7-9 were tested using three samples (a, b, c) of 5, 10, and 15 ppm of perfatty acid respectively. Example 10, containing no perfatty acid, was diluted to an equivalent formulation of Examples 7-9 containing perfatty acid. As can be seen from Table VII, significant kill occurred at 5 ppm for *S. aureus* using Examples 7-9. Significant kill occurred against *E. coli* at 10 ppm of perfatty acid in Examples 7-9. Example 10 (having no perfatty acid) did not produce any kill of either microorganism.

TABLE VII

Antimicrobial Efficacy of Examples 7-10

| | | Perfatty Acid Concentration | Log Kill | |
|---|---|---|---|---|
| Example | Sample | (ppm) | *S. aureus* | *E. coli* |
| 7 | a | 5 | >7.0 | 3.6 |
| | b | 10 | — | >7.2 |
| | c | 15 | — | >7.2 |
| 8 | a | 5 | >7.0 | 3.0 |
| | b | 10 | — | >7.2 |
| | c | 15 | — | >7.2 |
| 9 | a | 5 | >7.0 | <3.0 |
| | b | 10 | — | >7.2, 5.5 |
| | c | 15 | — | >7.2 |
| 10 | a | —[a] | 0 | — |
| | b | —[b] | — | 0 |

[a]Equivalent total product concentration as Examples 7, 8, 9 at 5 ppm perfatty acid.
[b]Equivalent total product concentration as Examples 7, 8, 9 at 15 ppm perfatty acid.

Example 11

The antimicrobial activity of percaprylic acid against *E. coli* was measured at a 30 second exposure at varying pH's. The formulation contained 94% water, 5% NAS 8D, and 1% percaprylic acid. The formulation was diluted in a buffer of 0.05M citrate and 0.05M potassium phosphate. The log kill of this formulation at increasing pH's is summarized in Table VIII. Samples containing 7 ppm and 25 ppm of percaprylic acid were tested. As Table VIII indicates, significant kill at 7 ppm occurred at a pH of 3.0. Significant kill levels were maintained at 25 ppm through a pH of 7.0.

TABLE VIII

Antimicrobial Efficacy of Percaprylic Acid against *E. coli*

| pH | Log Kill (Perfatty Concentration 7 ppm) | Log Kill (Perfatty Concentration 25 ppm) |
|---|---|---|
| 3.0 | >7.2 | >7.2 |
| 5.0 | <3.0 | >7.2 |
| 7.0 | <3.0 | >7.2 |
| 8.9 | — | <3.0 |
| 9.0 | <3.0 | — |

Examples 12–14

The compositions of Examples 12–14 were made to determine the limitations on cidal activity of compositions containing at least 30% acetic acid. Higher acetic acid formulations were also tested for their cidal activity. The composition of Example 14 was prepared with no coupler (NAS 8D). The compositional ingredients of Examples 12–14 are summarized below in Table IX.

TABLE IX

| Ingredient | Wt-% of Ingredient | | |
|---|---|---|---|
| | Example 12 | Example 13 | Example 14 |
| Acetic Acid | 30.0 | 50.0 | 50.0 |
| $H_2O_2$ (35%) | 30.0 | 15.0 | 15.0 |
| Dequest 2010 | 1.0 | 1.0 | 1.0 |
| $C_8$ Fatty Acid | 4.0 | 6.0 | 5.0 |
| NAS 8D (Spray Dried) | 5.0 | 5.0 | — |
| Distilled Water | 30.0 | 23.0 | 29.0 |

The antimicrobial efficacy of Examples 12–14 was determined using the procedure of the standard A.O.A.C. sanitizing test. The compositions of Examples 12–14 were diluted with 500 ppm hard water and employed at 25° C. The bacteria used in the test procedure were *S. aureus* and *E. coli*, and TGE plating medium was employed. Exposure time of the compositions to the bacteria was 30 seconds. The neutralizer employed in the testing procedure contained 0.1% thiosulfate, 1.0% peptone, and 0.025% catalase. The antimicrobial activity of Examples 12–14 is summarized in Table X below.

TABLE X

Cidal Activity of Examples 12–14

| Formulation | Concentration | pH | Log Reduction | |
|---|---|---|---|---|
| | | | *S. aureus* | *E. coli* |
| Example 12 | 1 oz:8 gal.$^a$ | 4.48 | >7.15 | >6.89 |
| | 1 oz:10 gal.$^b$ | 4.83 | >7.15 | >6.89 |
| | 1 oz:12 gal.$^c$ | 5.04 | >7.15 | 6.41 |
| | 1 oz:14 gal.$^d$ | 5.52 | >7.15 | 5.76 |
| | 1 oz:16 gal.$^e$ | 5.94 | >7.15 | 2.95 |
| Example 13 | 40 ppm Active | 4.16 | >7.15 | >6.89 |
| Example 14 | 40 ppm Active | 4.04 | >7.15 | >6.89 |

$^a$54.2 ppm peracid
$^b$43.3 ppm peracid
$^c$36.1 ppm peracid
$^d$31.0 ppm peracid
$^e$27.2 ppm peracid As Table X indicates, very low concentrations of combinations of peroxyacetic acid and peroxyfatty acid are very effective in killing bacteria. Also, Example 14 showed that the composition of the invention is antimicrobially effective without a hydrotrope coupler.

Example 15

Samples 1–10 were prepared to test the cidal activity of $C_2$, $C_5$, and $C_8$ peroxyacids, both alone and in various combinations. The peroxyacetic ($C_2$) acid was a production sample made by Ecolab Inc. under the trade name of Oxonia P3. Iodometric and ceric sulfate titrations on the day of microbiological testing gave a peroxyacetic acid concentration of 6.04%. The peroxyglutaric ($C_5$) acid was prepared by mixing 84 g of 35% hydrogen peroxide with 1 g of Dequest 2010 (Monsanto Corporation) and 15 g of glutaric acid. After standing for one week, the concentration of peroxyglutaric acid (by titration) had reached equilibrium. Titration on the day of microbiological testing gave a peroxyglutaric acid concentration of 11.42%. The peroxyoctanoic ($C_8$) acid was prepared by the method of W. E. Parker, C. Ricciuti, C. L. Ogg and D. Swern, J. Am. Chem. Soc. 77 4037 (1955), incorporated herein by reference. Several recrystalizations from low boiling petroleum ether gave the pure peroxyoctanoic acid. Titration on the day of microbiological testing showed the crystalline peroxyoctanoic acid to be 98–100% pure.

Microbiological test sample solutions were then made from each of the above peroxyacids. The Oxonia P3 (6.04% peroxyacetic acid) was first diluted 1:10 to obtain a working solution containing 6040 ppm of peroxyacetic acid. To obtain a 25 ppm use solution, 1.035 ml of this working solution was diluted to 250 ml with deionized water. To obtain a 50 ppm use solution, 2.07 ml of the working solution was similarly diluted to 250 ml. The peroxyglutaric acid (11.42% titratable peroxyglutaric acid) was diluted 1:20 with deionized water to obtain a 5710 ppm working solution of peroxyglutaric acid. To obtain a 25 ppm and a 50 ppm use solution, 1.095 ml and 2.189 ml were each diluted to 250 ml with deionized water. A solution of peroxyoctanoic acid was prepared by mixing 9.4144 g of deionized water with 0.5021 g of sodium octane sulfonate (a non-active coupler) and 0.1017 g of pure peroxyoctanoic acid. A 1:10 dilution with deionized water gave a 1000 ppm working solution of peroxyoctanoic acid. A 5 ppm use solution of peroxyoctanoic acid was obtained by diluting 1.25 ml of the working solution to 250 ml with deionized water.

Mixtures of the various peroxyacids were prepared in a similar fashion by adding the appropriate amount of each peroxyacid working solution to a volumetric flask and diluting to 250 ml with deionized water. In all cases, the sample solutions were tested soon after dilution to assure that no decomposition of the peroxyacids had occurred.

The microbiological testing followed the standard AOAC procedure, AOAC Official Methods of Analysis, 15th Edition, 1990, Germicidal and Detergent Sanitizing Action of Disinfectants, with the addition of McIlvaine's citric acid-phosphate buffer to maintain the pH of the sanitizer solution at pH 4.5. Contact time was 30 seconds. Testing was done in duplicate with the following results as summarized in Table XI.

TABLE XI

COOPERATIVE INTERACTION OF PEROXYACIDS

| Sample | $C_2$ (POAA[1]) | $C_5$ (POGA[2]) | $C_8$ (POOA[3]) | Log Reduction | |
|---|---|---|---|---|---|
| | | | | *S. aureus* | *E. coli* |
| 1 | 25 ppm | 0 | 0 | 0, 0.2 | 0.5, 0.5 |
| 2 | 50 ppm | 0 | 0 | 1.6, 1.4 | 1.9, 2.5 |
| 3 | 0 | 25 ppm | 0 | 0, 0 | 0.4, 0.4 |
| 4 | 0 | 50 ppm | 0 | 0.1, 0.1 | 1.4, 1.2 |
| 5 | 0 | 0 | 5 ppm | >6, 6.0 | 1.6, 1.6 |
| 6 | 25 ppm | 25 ppm | 0 | 1.2, 1.2 | 2.7, 2.9 |
| 7 | 25 ppm | 50 ppm | 0 | 2.1, 1.9 | >7, >7 |
| 8 | 0 | 25 ppm | 5 ppm | >6, >6 | 5.0, >7 |
| 9 | 0 | 50 ppm | 5 ppm | >6, >6 | >7, >7 |

TABLE XI-continued

COOPERATIVE INTERACTION OF PEROXYACIDS

| Sample | $C_2$ (POAA[1]) | $C_5$ (POGA[2]) | $C_8$ (POOA[3]) | Log Reduction S. aureus | E. coli |
|---|---|---|---|---|---|
| 10 | 25 ppm | 0 | 5 ppm | >6 | >7 |

[1]POAA = Peroxyacetic Acid, a $C_2$ acid
[2]POGA = Peroxyglutaric Acid, a $C_5$ acid
[3]POOA = Peroxyoctanoic Acid, a $C_8$ acid The above data clearly shows a much greater than additive antimicrobial activity (synergism) when the peroxyglutaric ($C_5$) acid was combined with peroxyoctanoic ($C_8$) acid (Samples 8 and 9). A similar but weaker effect was obtained when peroxyacetic ($C_2$) acid was combined with peroxyglutaric acid (Samples 6 and 7).

It should be noted that S. aureus is very sensitive to peroxyoctanoic acid, thus it is difficult to use this organism to demonstrate a synergism between peroxyoctanoic acid and other peroxyacids. However, E. coli is not particularly sensitive to any of the above single peroxyacids at the concentrations tested (see Samples 1–5), but combinations of peroxyglutaric acid with either peroxyacetic acid or peroxyoctanoic acid were surprisingly active. The combination of peroxyglutaric acid with peroxyoctanoic acid was particularly effective, and this combination displays a marked synergism (especially note the data for E. coli for Samples 8 and 9 and compare with the additive effects of Samples 3 or 4 with Sample 5). Thus, a combination of these two peroxyacids ($C_5$ and $C_8$) displays surprisingly effective bacterial kill against these representative gram positive and gram negative microorganisms at concentrations that provide real economic and safety benefits.

Example 16

Two formulas were prepared with the following ingredients as listed in Table XII.

TABLE XII

| Ingredient | Formula 1 (wt-%) | Formula 2 (wt-%) |
|---|---|---|
| $H_2O_2$ (35%) | 89 | 81 |
| Dequest 2010 | 1 | 1 |
| Glutaric Acid | 10 | 10 |
| Octanoic Acid | — | 3 |
| n-Octane Sulfonate | — | 5 |
| | 100 | 100 |

Each of the above formulas was allowed to stand at room temperature and equilibrate for seven days and was then titrated for total peroxyacid (calculated as peroxyglutaric acid). Formula 1 contained 7.49% peroxyglutaric acid, while Formula 2 contained 7.78% peroxyacids (calculated as peroxyglutaric acid but really a mixture of POGA and POOA).

The bacterial kill properties of the above two formulas were examined using E. coli as the test organism at room temperature in deionized water at 50 ppm total peroxyacid (as determined by titration of each formula, followed by appropriate dilution). The results are summarized in Table XIII below.

TABLE XIII

| | Bacterial Kill, E. coli, at 50 ppm Peroxyacid | | | |
|---|---|---|---|---|
| | Log Reduction pH | | | |
| | 2.2 | 4.0 | 6.0 | 8.0 |
| Formula 1 | 4.2 | 5.3 | 0.7 | 0.3 |

TABLE XIII-continued

| | Bacterial Kill, E. coli, at 50 ppm Peroxyacid | | | |
|---|---|---|---|---|
| | Log Reduction pH | | | |
| | 2.2 | 4.0 | 6.0 | 8.0 |
| Formula 2 | >6.9 | >7.2 | >7.2 | 3.2 |

Thus, 50 ppm of the peroxyacids in Formula 2 has a much more effective kill than 50 ppm of peroxyglutaric acid alone in Formula 1.

The solubilizer present in Formula 2 does not contribute significantly to bacterial kill. Thus, we have shown a simple way of enhancing the kill properties of peroxyglutaric acid. We merely formulate a product that contains hydrogen peroxide, glutaric acid, an appropriate fatty acid, a stabilizer and a solubilizer (for the fatty acid). On standing, this mixture will form an equilibrium mixture of peroxyacids. Mixtures of appropriate peroxyacids will be synergistic and effective at low concentrations. Glutaric acid has a very low odor, and monocarboxylic acids of chain length of $C_8$ or greater, especially at these lower concentrations, are also of low odor. Thus, we can readily formulate synergistic compositions that possess acceptably low odor even in the concentrated formula, but especially at use dilutions.

Example 17

A mixture of short chain fatty acids commercially available from Emery Corporation under the designation "EMERY 658" was employed in producing a sanitizing concentrate composition of the present invention. The "EMERY 658" acid is a mixture of caprylic acid ($C_8$) and capric acid ($C_{10}$). The perfatty acids were prepared by the method of Parker, et al., J. Amer. Chem. Soc., 77, 4037 (1955) which is incorporated by reference. The perfatty acid component (also containing 34% acetic acid and 10% hydrogen peroxide) was combined with a pre-made solution of 10.42% peracetic acid, a separate amount of acetic acid, water, and an n-octanesulfonate hydrotrope coupler (NAS 8D). The final composition of this Example was as listed in Table XIV.

Example 18

A second composition of the present invention was prepared as described in Example 17, except that caprylic acid ($C_8$) and capric acid ($C_{10}$) replaced some of the perfatty acid of Example 17. The concentration of peracetic acid was 5% while the concentration of perfatty acids was reduced to 1.5% (see Table XIV).

Example 19

The composition of Example 19 was prepared according to the procedure of Example 17, except that no peracetic acid or hydrogen peroxide was added to the composition. The acetic acid component was increased to 39 wt-% and the composition contained 5% perfatty acid (see Table XIV). Also, a chelating agent (Dequest 2010) was added to the composition.

Example 20

The composition of Example 20 was prepared the same as Example 19 except that caprylic acid and capric acid were added to the composition in addition to the percaprylic and percapric acid of Example 19. The composition contained 3.5% fatty acid and 1.5% perfatty acid (see Table XIV).

Example 21

Example 21 was prepared with only peracetic acid, acetic acid, hydrogen peroxide, and water. No perfatty acids or fatty acids were added to the composition of Example 21. The concentration of total peracid was about 5% and the acetic acid concentration was about 39% (see Table XIV).

Example 22

Example 22 was prepared the same as Example 20 except that no peracids were employed, only a mixture of fatty acids and acetic acid was used, along with water, NAS 8D, and Dequest 2010. The composition contained 5% fatty acid (see Table XIV).

0.025% catalase for peracetic acid/fatty acid (perfatty acid).

The antimicrobial activity of Examples 17–22 are summarized in Table XV. Examples 17 and 18 were tested using four samples (a,b,c,d) and Examples 19–22 were tested using two samples (a,b). As can be seen in Table XV, Examples 17–20 exhibited excellent kill (>log 6) of both *S. aureus* and *E. coli* at 50 ppm of peracid. Examples 21 and 22 (containing no perfatty acids) exhibited little or no activity. More specifically, Example 17 was tested at 1,000 and 500 ppm total product (50 and 25 ppm of both peroxyacetic acid and perfatty acid). At these low concentrations, the peracid combination gave a 6–7 log reduction in the bacterial count. Example 18 was tested at 1,000 and 500 ppm total

TABLE XIV

| Ingredient | Wt % of Ingredients | | | | | |
|---|---|---|---|---|---|---|
|  | Ex. 17 | Ex. 18 | Ex. 19 | Ex. 20 | Ex. 21 | Ex. 22 |
| Peracetic Acid (10.42% solution, 34% acetic acid, 10% $H_2O_2$) | 50 | 50 | — | — | 50 | — |
| Acetic Acid | 22 | 22 | 39 | 39 | 22 | 39 |
| Percaprylic Acid ($C_8$) | 3.75 | 1.125 | 3.75 | 1.125 | — | — |
| Percapric Acid ($C_{10}$) | 1.25 | 0.375 | 1.25 | 0.375 | — | — |
| Caprylic Acid ($C_8$) | — | 2.625 | — | 2.625 | — | 3.75 |
| Capric Acid ($C_{10}$) | — | 0.875 | — | 0.875 | — | 1.25 |
| NAS 8D | 10 | 10 | 10 | 10 | — | 10 |
| Water | 13 | 13 | 45 | 45 | 28 | 45 |
| Dequest 2010 | — | — | 1 | 1 | — | 1 |

Antimicrobial Efficacy of Examples 17–22

The compositions prepared according to Examples 17–22 were tested for their antimicrobial efficacy using the testing procedure of the standard A.O.A.C. sanitizing test. All of the samples tested of Examples 17–22 were made about 1 hour prior to testing. The bacteria used in the test procedure were *S. aureus* and *E. coli*. Distilled water was used to dilute the concentrate compositions of Examples 17–22 and the composition was employed at room temperature. The following neutralizers were employed in the test: 0.1% thiosulfate, peptone, 0.5% $K_2HPO_4$, 0.025% catalase for peracetic acid; chambers for fatty acid; 0.1% thiosulfate, peptone, product, and also had a 6–7 log reduction in the bacterial count. At the 500 ppm product concentration the product corresponds to 25 ppm of peroxyacetic acid and 7.5 ppm of perfatty acids. Example 19, at 1,000 ppm of total product (50 ppm of perfatty acid), completely killed all bacteria (greater than 7 log reduction). Example 20 also resulted in a complete kill using 1,000 ppm of total product (15 ppm perfatty acid). Example 21 contained no perfatty acid (only 50 ppm of peroxyacetic acid) and showed no activity against *S. aureus* and poor activity against *E. coli*. This is due to the fact that peroxyacetic acid is generally not effective at this level, and is generally used at concentrations greater than 100 ppm. Example 22, containing 5% fatty acid (30 ppm) and no perfatty acid at 1,000 ppm total product showed no activity toward either organism.

TABLE XV

| Ex. | Sample | Test Product Concentration (ppm) | POAA[1]/POFA[2]/FA[3] Concentration (ppm) | pH | $Log_{10}$ Kill | |
|---|---|---|---|---|---|---|
|  |  |  |  |  | S. aureus | E. coli |
| 17 | a | 1000 | 50/50/0 | 3.5 | 6.13 | >7.30 |
|  | b | 1000 | 50/50/0 | 3.5 | 6.52 | 7.30 |
|  | c | 500 | 25/25/0 | 3.68 | 6.63 | 7.00 |
|  | d | 500 | 25/25/0 | 3.68 | 6.78 | 7.30 |
| 18 | a | 1000 | 50/15/35 | 3.52 | 7.18 | 7.30 |
|  | b | 1000 | 50/15/35 | 3.52 | 6.63 | 6.90 |
|  | c | 500 | 25/7.5/17.5 | 3.68 | 6.70 | 6.76 |
|  | d | 500 | 25/7.5/17.5 | 3.68 | 7.18 | 7.00 |
| 19 | a | 1000 | 0/50/0 | 3.5 | >7.18 | >7.30 |
|  | b | 1000 | 0/50/0 | 3.5 | >7.18 | >7.30 |
| 20 | a | 1000 | 0/15/35 | 3.5 | >7.18 | >7.30 |
|  | b | 1000 | 0/15/35 | 3.5 | >7.18 | >7.30 |
| 21 | a | 1000 | 50/0/0 | 3.49 | NMA[4] | 3.48 |
|  | b | 1000 | 50/0/0 | 3.49 | NMA | 3.80 |
| 22 | a | 1000 | 0/0/30 | 3.46 | NMA | NMA |

TABLE XV-continued

| Ex. | Sample | Test Product Concentration (ppm) | POAA[1]/POFA[2]/FA[3] Concentration (ppm) | pH | Log₁₀ Kill S. aureus | E. coli |
|---|---|---|---|---|---|---|
| | b | 1000 | 0/0/30 | 3.46 | NMA | NMA |

[1]POAA = Peroxyacetic Acid
[2]POFA = Peroxyfatty Acid
[3]FA = Fatty Acid
[4]NMA = No measurable activity

Examples 23–26

Examples 23–26 were prepared by substantially the same procedure as the previous Examples, except that hydrogen peroxide ($H_2O_2$) was mixed with acetic acid and $C_{8-10}$ fatty acids (Emery 658) to make the peracids of the composition. Table XVI summarizes the components and amounts of the various compositions of Examples 23–26 which were made.

TABLE XVI

| | Peracid Test Formulations | | | |
|---|---|---|---|---|
| Ingredient | Ex. 23 | Ex. 24 | Ex. 25 | Ex. 26 |
| Acetic Acid | 44 | 39 | 34 | 49 |
| H₂O₂ (35%) | 40 | 40 | 40 | 40 |
| Dequest 2010 | 1 | 1 | 1 | 1 |
| NAS 8D | 10 | 10 | 10 | 10 |
| Emery 658 | 5 | 10 | 15 | — |

Peracid Stability, Cidal Activity of Examples 23–26

Each of Examples 23–26 were tested for peracid stability and cidal activity using the A.O.A.C. sanitizing test against S. aureus and E. coli at room temperature with the formulations diluted in distilled water. Tables XVII–XX show the cidal activity of each formulation. Generally all of the formulations reached maximum peracid formation within about 12 days. All of the formulations obtained about 12.5% peracid except Example 25 (15% fatty acid) which obtained about 11.5% peracid.

Table XVII summarizes the cidal activity of Example 23 in which the composition was measured for cidal activity on the first day up to day 33. At 250 ppm of total product, there were about 4–5 ppm of perfatty acid and about 20 ppm of peracetic acid as determined by carbon 13 NMR spectroscopy of the concentrate. The results are summarized in Table XVII.

TABLE XVII

Peracid Stability, Cidal Activity of Example 23

| Day | Peracid Percent | Test[a] Concentration | Test pH | Ave. Log Reduction S. aureus | E. coli |
|---|---|---|---|---|---|
| 1 | 4.28 | 250 ppm | 3.92 | 6.28 | NMA[b] |
| 6 | 11.00 | 250 ppm | 3.91 | >7.38 | >7.18 |
| 8 | 11.08 | 250 ppm | 3.86 | >7.11 | >7.12 |
| 12 | 12.43 | 250 ppm | 3.83 | >7.18 | 6.96 |
| 15 | 12.74 | 250 ppm | 3.88 | 6.95 | — |
| 33 | 10.18 | 250 ppm | 3.83 | 5.18 | 6.34 |

[a]ppm total product
[b]No measurable activity

The cidal activity of Example 24 is summarized in Table XVIII below. The peracetic acid concentration at 250 ppm of product was about 20–21 ppm and the concentration of perfatty acid was about 11 ppm. The concentration of peracetic acid at 50 ppm of product was about 4 ppm and the concentration of perfatty acid was about 2 ppm.

TABLE XVIII

Peracid Stability, Cidal Activity of Example 24

| Day | Peracid Percent | Test[a] Concentration | Test pH | Ave. Log Reduction S. aureus | E. coli |
|---|---|---|---|---|---|
| 1 | 4.88 | 250 ppm | 3.95 | >7.60 | NMA[b] |
| 6 | 10.62 | 250 ppm | 3.92 | >7.38 | >7.18 |
| 8 | 11.61 | 250 ppm | 3.98 | >7.11 | >7.12 |
| 12 | 12.47 | 250 ppm | 3.91 | >7.18 | >7.23 |
| 15 | 12.00 | 250 ppm | 3.95 | 6.95 | — |
| | | 120 ppm | 4.18 | >7.13 | — |
| | | 50 ppm | 4.41 | 6.39 | — |
| 33 | 10.49 | 250 ppm | 3.85 | 5.20 | 6.22 |

[a]ppm total product
[b]No measurable activity

The cidal activity of Example 25 is summarized in Table XIX below. At 250 ppm of product the peracetic acid concentration was about 19 ppm and the perfatty acid concentration was about 14 ppm.

TABLE XIX

Peracid Stability, Cidal Activity of Example 25

| Day | Peracid Percent | Test[a] Concentration | Test pH | Ave. Log Reduction S. aureus | E. coli |
|---|---|---|---|---|---|
| 1 | 4.84 | 250 ppm | 3.90 | >7.60 | NMA[b] |
| 6 | 9.81 | 250 ppm | 3.96 | >7.38 | >7.18 |
| 8 | 10.99 | 250 ppm | 3.96 | >7.11 | >7.12 |
| 12 | 11.47 | 250 ppm | 3.94 | >7.18 | >7.23 |
| 15 | 11.48 | 250 ppm | 3.96 | 6.83 | — |
| 33 | 10.49 | 250 ppm | 3.95 | 5.25 | 6.53 |

[a]ppm total product
[b]No measurable activity

The cidal activity of Example 26 is summarized in Table XX below. At 250 ppm of product there was about 27 ppm of peracetic acid. At 1000 ppm of product there was about 108 ppm of peracetic acid. No fatty acid was employed in the composition of Example 26.

TABLE XX

Cidal Activity of Example 26

| Day | Peracid Percent | Test[a] Concentration | Test pH | Ave. Log Reduction S. aureus | E. coli |
|---|---|---|---|---|---|
| 5 | 10.95 | 250 ppm | 3.90 | NMA[b] | NMA |
| 7 | 12.03 | 1000 ppm | 3.50 | 4.60 | >7.12 |
| 11 | 12.44 | 1000 ppm | 3.49 | 6.38 | 6.64 |
| 14 | 12.53 | 1000 ppm | 3.50 | 4.17 | — |
| 32 | 10.77 | 1000 ppm | 3.45 | 4.77 | 6.44 |

[a]ppm total product
[b]No measurable activity

When comparing the formulations containing fatty acid (Tables XVII–XIX), poor activity was measured against E. coli one day after being formulated. Since the total peracid values were low, more fatty acid was present and gram negative bacteria tend to be less sensitive than gram positive bacteria to the $C_8$-$C_{10}$ fatty acids. However, as more peracid developed over the days indicated, increased cidal activity against E. coli was observed. Table XX indicates that to obtain acceptable activity (greater than or equal to 5 log reduction) using only peracetic acid, the peracetic acid must be tested over 100 ppm active. Secondly, this oxidizing compound is more effective against *E. coli* than *S. aureus*.

Generally all the formulations containing fatty acid remain stable after about 1 month. This was confirmed by repeated testing over time at 250 ppm total product for each formulation in which greater than 5 log reductions were measured against *S. aureus* and *E. coli*.

Examples 27–32

The cidal activity of a two-component system containing both peracetic acid and fatty acid was investigated using the A.O.A.C. sanitizing test. Table XXI shows the product formulations examined. The test samples include controls showing cidal activity of NAS 8D as well as fatty acid kill against *S. aureus*. All the samples were tested in distilled water.

TABLE XXI

| Ingredient | Wt % Ingredient | | | | | |
| --- | --- | --- | --- | --- | --- | --- |
| | Ex. 27 | Ex. 28 | Ex. 29 | Ex. 30 | Ex. 31 | Ex. 32 |
| Base 1[a] | 80 | 80 | 80 | 80 | — | — |
| Base 2[b] | — | — | — | — | 80 | 80 |
| NAS 8D | 10 | — | 10 | 10 | 10 | 10 |
| Octanoic Acid | — | — | 10 | — | — | 10 |
| Emery 658 | — | — | — | 10 | 10 | — |
| $H_2O$ | 10 | 20 | — | — | — | — |

[a] $H_2O_2$, 35%; acetic acid, 35%; Dequest 2010, 1%; $H_3PO_4$ (85%), 29%.
[b] Acetic acid, 35%; Dequest 2010, 1%; $H_3PO_4$ (85%), 29%; $H_2O$, 35%.

Table XXII shows the activity measurement of each of Examples 27–32 at various test concentrations. When testing the peracetic acid formulation of Examples 27 and 28 (having no fatty acid), biocidal activity occurred only at 100 ppm or greater. Cidal activity (greater than 4 log reduction) was measured at a minimal concentration of 10 ppm peracid with fatty acid in the system (Example 29). At 10 ppm peracid, the composition containing Emery 658 (Example 30) had better activity than the system containing only $C_8$ (octanoic) fatty acid (Example 29). In the fatty acid controls having no oxidant (Examples 31 and 32), the Emery 658 had more cidal activity than the $C_8$ fatty acid. At total product test concentrations equivalent to 10 or 25 ppm peracid, the fatty acid in the system of Example 31 did not have significant cidal activity. Example 32 did not have significant cidal activity at any test concentration.

TABLE XXII

| | Peracid Cidal Activity Against *S. aureus* | | | |
| --- | --- | --- | --- | --- |
| Example | Peracid (%) | Concentration (ppm Peracid) | Test pH | Log[a] Reduction |
| 27 | 7.02 | 50 | 2.79 | NMA[b] |
| | | 100 | 2.54 | 5.45 |
| | | 150 | 2.41 | >7.70 |
| 28 | 6.25 | 50 | 2.76 | NMA |
| | | 100 | 2.52 | 4.51 |
| | | 150 | 2.40 | 5.84 |
| 29 | 9.32 | 10 | 3.52 | 4.22 |
| | | 25 | 3.16 | >7.70 |
| | | 50 | 2.90 | >7.70 |
| 30 | 9.73 | 10 | 3.50 | 6.82 |
| | | 25 | 3.19 | 7.55 |
| | | 50 | 2.88 | >7.70 |
| 31 | — | —[c] | 3.53 | 0.70 |
| | | —[c-1] | 3.18 | 1.04 |
| | | —[c-2] | 2.88 | 4.07 |
| 32 | — | —[d] | 3.51 | 0.93 |
| | | —[d-1] | — | 0.66 |

TABLE XXII-continued

| | Peracid Cidal Activity Against *S. aureus* | | | |
| --- | --- | --- | --- | --- |
| Example | Peracid (%) | Concentration (ppm Peracid) | Test pH | Log[a] Reduction |
| | | —[d-2] | — | 0.97 |

[a] Average of duplicate testing.
[b] No measurable activity.
[c] Same total product concentration as Example 30 @ 10 ppm peracid (about 100 ppm product).
[c-1] Same total product concentration as Example 30 @ 25 ppm peracid (about 250 ppm product).
[c-2] Same total product concentration as Example 30 @ 50 ppm peracid (about 500 ppm product).
[d] Same total product concentration as Example 29 @ 10 ppm peracid (about 100 ppm product).
[d-1] Same total product concentration as Example 29 @ 25 ppm peracid (about 250 ppm product).
[d-2] Same total product concentration as Example 29 @ 50 ppm peracid (about 500 ppm product).

The cidal activity of a peracetic acid/fatty acid system was measured comparing freshly made formulations to month-old formulations of Examples 30 and 31. These formulations are shown in Table XXIII which compares the titration values of month-old formulations to the same freshly prepared. Table XXIV shows the cidal activity of month-old and fresh formulations of Examples 29 and 30.

TABLE XXIII

| | Peracid Titration Values | | | |
| --- | --- | --- | --- | --- |
| | Ex. 29 | Ex. 30 | Ex. 29 | Ex. 30 |
| Date formulated | Month-Old | Month-Old | Fresh | Fresh |
| % $H_2O_2$ | 2.15 | 2.07 | 1.99 | 1.99 |
| % Peracid | 5.37 | 5.35 | 4.85 | 4.86 |
| % Total $O_2$ | 2.14 | 2.10 | 1.96 | 1.96 |

TABLE XXIV

| | Peracid Cidal Activity Against *S. aureus* | | | |
| --- | --- | --- | --- | --- |
| Example | Peracid (%) | Test Concentration (ppm Peracid) | Test pH | Log[a] Reduction |
| 29 (Month-Old) | 5.37 | 10 | 3.46 | NMA[b] |
| | | 25 | 3.07 | >7.48 |
| 29 (Fresh) | 4.85 | 10 | 3.34 | 5.07 |
| | | 25 | 2.97 | 7.30 |
| 30 (Month-Old) | 5.35 | 10 | 3.52 | 5.29 |
| | | 25 | 3.04 | 7.24 |
| 30 (Fresh) | 4.86 | 10 | 3.42 | NMA[c]/ |
| | | 25 | 2.99 | 7.48 |

[a] Average of duplicate testing.
[b] No measurable activity (3.68 log reduction).
[c] Duplicate testing in which only one sample exhibited cidal activity.

As can be seen from Table XXIV, cidal activity in the peracetic acid/fatty acid system occurs at test concentrations as low as 10 or 25 ppm peracid. Mixed results occurred at 10 ppm peracid between the month-old and fresh formulations of Examples 29 and 30, however, increasing the concentration to 25 ppm resulted in a uniform kill activity (>7 log reduction).

An additional test was run to determine how quickly compounds exhibiting cidal activity are formed upon adding fatty acid to a peracetic acid system. Examples 27, 30 and were tested. Examples 27 and 30 were formulated the day before testing and were day-old samples. Another test sample of Example 30 was formulated immediately prior to testing. Example 31 containing Base 2 (no $H_2O_2$) was used to show cidal activity from the fatty acid at low test concentrations. Table XXV shows the cidal activity of each Example in distilled water against *S. aureus*.

TABLE XXV

| | Cidal Activity Against *S. aureus* | | | |
|---|---|---|---|---|
| Example | Age | ppm Peracid | Test pH | Log[a] Reduction |
| 27 | 1 day | 50 | 2.94 | NMA[b] |
| | | 100 | 2.71 | 6.60 |
| 30 | 1 day | 10 | 3.68 | 7.02 |
| | | 25 | 3.35 | >7.20 |
| 30 | fresh | 10 | 3.76 | NMA |
| | | 25 | 3.32 | NMA |
| 31 | 22 days | —[c] | 3.74 | NMA |
| | | —[d] | — | NMA |

[a] Average of duplicate testing.
[b] No measurable activity.
[c] Equivalent total product concentration as Example 30 (day old) @ 10 ppm peracid.
[d] Equivalent total product concentration as Example 30 (day old) @ 25 ppm peracid.

The data from Table XXV suggests that the formation of compounds containing cidal activity when adding fatty acid to a peracetic acid system is not immediate, but does occur within a day. The formation of compounds exhibiting cidal activity occurred within a day after adding fatty acid to the peracetic acid system as in Example 30 with cidal activity occurring at a concentration as low as 10 ppm peracid. Thus, the cidal activity is not due to the mere combination of fatty acid and peroxyacetic acid, but the fatty acid must be converted to the perfatty acid before substantially enhanced cidal activity occurs.

The foregoing discussion and Examples are illustrative of the invention. However, since many embodiments of the invention can be made without departing from the spirit and scope of the invention, the invention resides in the claims hereinafter appended.

We claim:

1. An aqueous peroxyacid antimicrobial composition consisting essentially of:
   (a) at least about 10 parts per million (ppm) of peroxyglutaric acid; and
   (b) at least about 1 ppm of a peroxyacid selected from the group consisting of a $C_6$-$C_{18}$ aliphatic peroxyacid, and mixtures thereof;
   wherein the aqueous composition has a pH in the range of about 2 to 8.

2. The aqueous composition of claim 1 wherein said $C_6$-$C_{18}$ peroxyacid is an aliphatic peroxyfatty acid, or an aliphatic monoperoxy- or diperoxydicarboxylic acid.

3. The aqueous composition of claim 1 wherein said $C_6C_{18}$ peroxyacid is selected from the group consisting of peroxyoctanoic acid, peroxydecanoic acid, monoperoxy- or diperoxyadipic acid, monoperoxy- or diperoxysebacic acid, and mixtures thereof 4. The aqueous composition of claim 1 further containing at least about 1 ppm of a hydrotrope coupling agent.

5. The aqueous composition of claim 1 wherein the weight ratio of said $C_5$ peroxyacid to said peroxyacid of (b) is about 20:1 to 1:10.

6. The aqueous composition of claim 1 further containing at least about 10 ppm of a carboxylic acid selected from the group consisting of glutaric acid, a $C_6$-$C_{18}$ aliphatic carboxylic acid, and mixtures thereof.

7. The aqueous composition of claim 6 wherein said $C_6$-$C_{18}$ carboxylic acid is selected from the group consisting of octanoic acid, decanoic acid, adipic acid, sebacic acid, and mixtures thereof.

8. The aqueous composition of claim 1 further comprising at least about 1 ppm of hydrogen peroxide.

9. An aqueous peroxyacid antimicrobial sanitizing composition consisting essentially of:
   (a) about 10 to 75 parts per million (ppm) of peroxyglutaric acid;
   (b) about 1 to 25 ppm of a peroxyacid of the structure $R_1$—$CO_3H$ wherein $R_1$ is an aliphatic hydrocarbon chain having about 5 to 17 carbon atoms;
   (c) about 1 to 200 ppm of a hydrotrope coupling agent; and
   (d) about 2 to 200 ppm of hydrogen peroxide;
   wherein the aqueous composition has a pH in the range of about 3 to 7.

10. The concentrate composition of claim 7 wherein said peroxyacid of (b) is a peroxyfatty acid having about 8 to 12 carbon atoms per molecule.

11. The aqueous composition of claim 10 wherein said peroxyfatty acid is peroxyoctanoic acid, peroxydecanoic acid, or mixtures thereof.

12. The aqueous composition of claim 9 wherein said hydrotrope is n-octanesulfonate.

13. The aqueous composition of claim 10 further containing about 10 to 800 ppm of a carboxylic acid selected from the group consisting of a fatty acid, glutaric acid, and mixtures thereof.

14. The aqueous composition of claim 3 wherein said fatty acid is octanoic acid, decanoic acid, or mixtures thereof.

15. The composition of claim 1 further containing a chelating agent for binding polyvalent metal cations.

16. The composition of claim 15 wherein said chelating agent is 1-hydroxyethylidene-1,1-diphosphonic acid.

17. The composition of claim 9 further containing a chelating agent for binding polyvalent metal cations.

18. The composition of claim 17 wherein said chelating agent is 1-hydroxyethylidene-1,1-diphosphonic acid.

* * * * *